United States Patent [19]

Roth et al.

[11] 4,134,895

[45] Jan. 16, 1979

[54] IMIDYL-BENZENEDICARBOXYLIC ACID DERIVATIVES

[75] Inventors: Martin Roth, Basel; Vratislav Kvita, Muttenz; Gerd Greber, Binningen, all of Switzerland

[73] Assignee: Ciba-Geigy Corporation, Ardsley, N.Y.

[21] Appl. No.: 696,347

[22] Filed: Jun. 15, 1976

[30] Foreign Application Priority Data

Jun. 18, 1975 [CH] Switzerland .................. 7952/75

[51] Int. Cl.$^2$ ................. C07D 207/44; C07D 403/02
[52] U.S. Cl. ...................... 260/326.41; 260/326 A; 260/326 C; 260/326 N; 260/326.26; 260/326.27; 260/326.29; 260/326.5 B; 260/326.5 FM; 526/263; 528/322
[58] Field of Search ............ 260/326.5 FM, 326.41, 260/326.43, 326.34, 326.26, 78 UA, 47 UA; 526/263

[56] References Cited

U.S. PATENT DOCUMENTS

| B 497,490 | 3/1976 | D'Alelio | 260/78 UA |
|---|---|---|---|
| 2,650,215 | 8/1953 | Strain | 260/78 UA |
| 2,726,981 | 12/1955 | Wolf et al. | 260/326.5 FM |
| 2,850,351 | 9/1958 | Moore et al. | 260/326.26 |
| 2,890,207 | 6/1959 | Kraeman | 260/78 UA |
| 2,890,260 | 6/1959 | Kraeman | 260/78 UA |
| 2,906,738 | 9/1959 | Goldberg | 260/78 UA |
| 2,958,672 | 11/1960 | Goldberg | 260/78 UA |
| 2,962,504 | 11/1960 | Walker et al. | 260/326.5 FM |
| 2,971,944 | 2/1961 | Chow et al. | 260/78 UA |
| 3,039,860 | 6/1962 | Andress et al. | 260/326.41 |
| 3,074,915 | 1/1963 | Chow | 260/78 UA |
| 3,127,414 | 3/1964 | Cole et al. | 260/78 UA |
| 3,352,832 | 11/1967 | Barr et al. | 260/78 UA |
| 3,435,003 | 3/1969 | Craven | 260/78 UA |
| 3,465,001 | 9/1969 | Bolhofer et al. | 260/326.41 |
| 3,465,002 | 9/1969 | Bolhofer et al. | 260/326.41 |
| 3,506,624 | 4/1970 | Behrens | 260/78 UA |
| 3,522,271 | 7/1970 | Kalel | 260/78 UA |
| 3,538,114 | 11/1976 | Himmele et al. | 260/326.5 FM |
| 3,549,725 | 12/1970 | Rose et al. | 260/78 UA |
| 3,660,408 | 5/1972 | Ackerman | 260/326.5 FM |
| 3,666,720 | 5/1972 | Nield et al. | 260/78 UA |
| 3,766,142 | 10/1973 | Nield et al. | 260/78 UA |
| 3,810,913 | 5/1974 | Relles | 260/326.26 |
| 3,816,451 | 6/1974 | Crovetti et al. | 260/326.5 FM |
| 3,929,713 | 12/1975 | D'Alelio | 260/78 UA |
| 4,043,986 | 8/1977 | Gruffaz et al. | 260/47 UA |

FOREIGN PATENT DOCUMENTS

| 1401621 | 4/1965 | France | 260/326.26 |
|---|---|---|---|
| 1594934 | 7/1970 | France | 260/326 |
| 47-14747 | 11/1969 | Japan | 260/326.26 |
| 47-16061 | 5/1972 | Japan | 260/326.26 |
| 47-14745 | 5/1972 | Japan | 260/326.26 |

*Primary Examiner*—José Tovar
*Assistant Examiner*—Mary C. Lee
*Attorney, Agent, or Firm*—Luther A. R. Hall

[57] ABSTRACT

New imidyl-benzenedicarboxylic acid derivatives, in particular 5-maleimidyl-isophthalic acid derivatives and 5-(nadic acid-imidyl)-isophthalic acid derivatives, and a process for their manufacture are described. These imidyl-benzenedicarboxylic acid derivatives are suitable for the manufacture of crosslinkable polymers, above all polycondensation and polymerization products, which are distinguished by good processability and good solubility in the customary organic solvents.

7 Claims, No Drawings

IMIDYL-BENZENEDICARBOXYLIC ACID DERIVATIVES

The present invention relates to new imidyl-benzenedicarboxylic acid derivatives and a process for their manufacture.

The new imidyl-benzenedicarboxylic acid derivatives correspond to the formula Ia or Ib

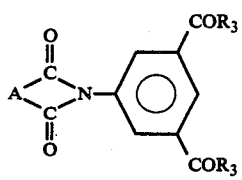

(Ia)

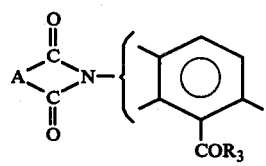

(Ib), wherein A represents a radical of the formula

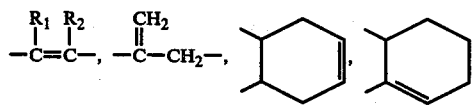

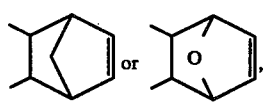

$R_1$ and $R_2$ independently of one another represent hydrogen, chlorine or bromine and $R_3$ represents a chlorine atom, a hydroxyl group, an unsubstituted or substituted phenoxy group, an alkoxy group with 1 to 18 carbon atoms or a $-O^-M^+$ group, in which $M^+$ denotes an alkali metal cation, a trialkylammonium cation with 3-24, and especially with 3-12, carbon atoms or a quaternary ammonium cation.

The new imidyl-benzenedicarboxylic acids of the formula Ia and Ib can be manufactured, according to the invention, by reacting an amine of the formula IIa or IIb

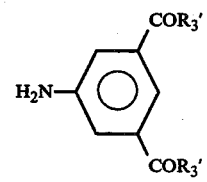

(IIa)

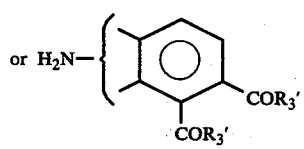

(IIb)

in at least the stoichiometric amount with an anhydride of the formula III

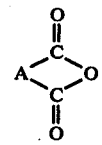 (III)

to give a compound of the formula IVa or IVb

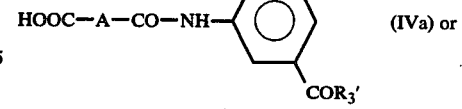 (IVa) or

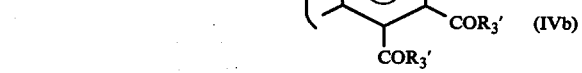 (IVb)

wherein A has the indicated meaning and $R_3'$ denotes a hydroxyl group, an unsubstituted phenoxy group or a substituted phenoxy group which is free from electronegative substituents, an alkoxy group with 1-18 carbon atoms or a $-O^-M^+$ group, subsequently cyclising the compound of the formula IVa or IVb and optionally converting the resulting compound of the formula Ia or Ib into another derivative, according to the definition, of the formula Ia or Ib.

A preferably represents the radical

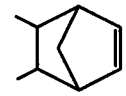

or the radical $-CH=CH-$.

If the $R_3$'s represent substituted phenoxy groups, these are, in particular, phenoxy groups which are substituted by nitro groups or alkyl or alkoxy groups with 1 or 2 carbon atoms or by halogen atoms, above all chlorine of fluorine, such as the 2-, 3- or 4-nitrophenoxy group, 2,4- or 3,5-dinitrophenoxy group, 3,5-dichlorophenoxy group, the pentachlorophenoxy group or the 2-methyl- or 2-methoxy-phenoxy group. According to the definition, substituted phenoxy groups $R_3'$ are free from electronegative substituents, such as nitro groups or halogen atoms. End products of the formula Ia or Ib wherein the $R_3$'s denote phenoxy groups containing electronegative substituents can be manufactured — as indicated further below — from the corresponding free acids ($R_3 = -OH$), from the acid chlorides ($R_3 = -Cl$) or by trans-esterification.

Alkoxy groups $R_3$ and $R_3'$ can be straight-chain or branched. Examples which may be mentioned are: the methoxy, ethoxy, n-propoxy, isopropoxy, n-butoxy, tert.-butoxy, hexyloxy, octoxy, decyloxy, dodecyloxy, tetradecyloxy and octadecyloxy group.

If $R_3$ or $R_3'$ denote a $-O^-M^+$ group, $M^+$ represents, for example, the lithium, sodium, potassium, trimethylammonium, triethylammonium, methyl-diethylammonium, tri-n-octylammonium, benzyltrimethylammonium or tetramethylammonium cation. $M^+$ preferably represents the sodium cation.

Compounds of the formula Ib and, in particular, those of the formula Ia, wherein A denotes the radical

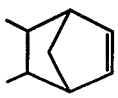

or the radical —CH═CH— and R₃ denotes a chlorine atom, an unsubstituted phenoxy group or an alkoxy group with 1–12, and especially 1–4, carbon atoms, are preferred.

Compounds of the formula Ia wherein A denotes the radical

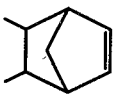

or the radical —CH═CH— and R₃ represents a chlorine atom are very particularly preferred.

The starting materials of the formulae IIa, IIb and III are known or can be manufactured in a manner which is in itself known.

Examples which may be mentioned of suitable amines of the formula IIa and IIb are: 3- and 4-aminophthalic acid, 5-aminoisophthalic acid and the corresponding disodium salts and triethylammonium salts, 3- and 4-aminophthalic acid dimethyl, diethyl, di-n-octyl and diphenyl esters and 5-amino-isophthalic acid dimethyl, diethyl, di-n-octyl and diphenyl esters.

Amines of the formula IIb and especially those of the formula IIa wherein $R_3'$ denotes an unsubstituted phenoxy group or an alkoxy group with 1–12, and above all 1–4, carbon atoms are preferably used. Amines of the formula IIb and, above all, amines of the formula IIa wherein $R_3'$ represents a —O⁻M⁺ group and M⁺ represents an alkali metal cation, especially the Na cation, are particularly preferentially used in the process according to the invention.

The aminobenzenedicarboxylic acids of the formula IIa and IIb, and their derivatives, can be employed as such or can be manufactured in situ by reduction of the corresponding nitrobenzenedicarboxylic acids, or derivatives thereof, and used further without intermediate isolation. It is also possible to use mixtures of different amines of the formula IIa or IIb, for example mixtures of 3- and 4-aminophthalic acid or derivatives thereof.

Examples which may be mentioned of suitable anhydrides of the formula III are: maleic anhydride, itaconic anhydride, chloromaleic anhydride, 2,3-dichloromaleic anhydride, 2,3-dibromomaleic anhydride, 4- and 2-cyclohexene-1,2-dicarboxylic acid anhydride, 3,6-endomethylene-1,2,3,6-tetrahydro-phthalic anhydride (nadic anhydride) and 3,6-endoxo-1,2,3,6-tetrahydrophthalic anhydride. Nadic anhydride and maleic anhydride are preferred.

The reaction of the amines of the formula IIa and IIb with the anhydrides of the formula III can be carried out in the melt by heating the reactants to temperatures of up to about 150° C., or in an aqueous, aqueous-organic or organic medium, in which case the reaction is appropriately carried out at temperatures between about 0° C. and 50° C., especially between about 15° C. and 25° C. The reaction is preferably carried out in an aqueous or aqueous-organic medium.

Appropriately, the anhydride of the formula III is employed in the stoichiometric amount or in a slight excess over the amine of the formula IIa or IIb, for example in an up to about 20% molar excess.

Organic solvents which can be used are, above all, aprotic organic solvents. Examples of suitable aprotic organic solvents are: optionally chlorinated aliphatic or aromatic hydrocarbons, such as benzene, toluene, methylene chloride, chloroform, carbon tetrachloride, 1,1,2-trichloroethane, 1,2-dichloroethylene and chlorobenzene; aliphatic and cycloaliphatic ketones, such as acetone, methyl ethyl ketone, cyclopentanone and cyclohexanone; cyclic ethers, such as tetrahydrofurane, tetrahydropyrane and dioxane; cyclic amides, such as N-methyl-2-pyrrolidone, N-acetyl-2-pyrrolidone and N-methyl-ε-caprolactam; N,N-dialkylamides of aliphatic monocarboxylic acids with 1–3 carbon atoms in the acid part, such as N,N-dimethylformamide, N,N-dimethylacetamide, N,N-diethylacetamide and N,N-dimethylmethoxyacetamide; alkyl esters of aliphatic monocarboxylic acids with a total of 2–6 carbon atoms, such as formic acid methyl, ethyl or n-butyl ester or acetic acid methyl, ethyl or n-butyl ester; hexamethylphosphoric acid triamide (hexametapol); N,N,N',N'-tetramethylurea; tetrahydrothiophene dioxide (sulpholane) and dialkylsulphoxides, such as dimethylsulphoxide and diethylsulphoxide.

Mixtures of solvents of this type can also be employed. Preferred solvents are dioxane and methylene chloride.

After the reaction has ended, the amide-acid derivatives of the formula IVa or IVb are isolated in the customary manner by filtration or by stripping off the solvent, and optionally purified, for example by washing with water and/or with suitable solvents, such as methanol, dioxane, diethyl ether, methylene chloride and chloroform, or by recrystallisation or extraction with suitable organic solvents, such as ethyl acetate. Solvent mixtures can also be used.

The amide-acids of the formula IVa or IVb can, however, also be cyclised direct, without intermediate isolation, to give the imidyl compounds of the formula Ia or Ib. The cyclisation of the amide-acids to give compounds of the formula Ia or Ib can be carried out, in a manner which is in itself known, chemically, that is to say using catalysts which are in themselves known for forming imides and/or using dehydrating agents, and/or by the action of heat.

The cyclisation is generally carried out at temperatures between about 40 and 120° C., preferably 70–90° C., with the addition of suitable catalysts and/or dehydrating agents and optionally in the presence of an aprotic organic solvent.

Dehydrating agents which can be used are, above all, anhydrides of aliphatic monocarboxylic acids which have 2–5 carbon atoms and are optionally substituted by halogen atoms or alkyl groups, such as acetic anhydride, propionic anhydride, butyric anhydride and valeric anhydride and trichloro-, trifluoro-, trimethyl-, triethyl- and tri-n-butyl-acetic anhydride. Acetic anhydride is the preferred dehydrating agent.

Catalysts which can be used are, for example, alkaline earth metal salts of alkali metal salts of aromatic monocarboxylic acids or of aliphatic monocarboxylic acids with 1–4 carbon atoms, such as sodium benzoate, sodium salicylate, calcium formate and sodium formate, calcium acetate, magnesium acetate, sodium acetate and potassium acetate and sodium propionate; bases, such as trimethylamine and triethylamine, or nickel salts or nickel complexes, such as nickel-2 acetate or nickel acetylacetonate. Preferred catalysts are sodium acetate, nickel-2 acetate and triethylamine.

Under certain circumstances it can be advantageous additionally to use an aprotic organic solvent, above all benzene or toluene, in the cyclisation. The cyclisation to give compounds of the formula Ia and Ib can also be carried out by means of heat, by heating to temperatures of about 40° C. to 150° C.

The compounds of the formula Ia or Ib which are obtained after the cyclisation can, if desired — and depending on the nature of the amines used — be converted in a manner which is in itself known into other derivatives, according to the definition, of the formula Ia or Ib, for example as follows:

Acid chlorides ($R_3$ = —Cl) by reaction of compounds of the formula Ia or Ib wherein $R_3$ = —OH or —O$^-$M$^+$ with suitable chlorinating agents, such as thionyl chloride, oxalyl chloride and phosgene, Esters ($R_3$ = unsubstituted or substituted phenoxy or alkoxy) by reaction of compounds of the formula Ia or Ib wherein $R_3$ = —OH or —Cl with alcohols $R_3$OH; or by trans-esterification of compounds of the formula Ia or Ib wherein $R_3$ = unsubstituted or substituted phenoxy or alkoxy and Salts ($R_3$ = —O$^-$M$^+$) by reaction of the free acids with corresponding bases, such as NaOH.

It is also posssible to convert compounds of the formula Ia or Ib wherein A represents —CH=CH— into compounds of the formula Ia or Ib wherein A represents the group

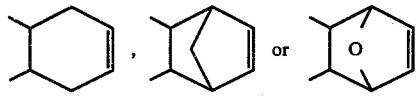

by an addition reaction with 1,3-butadiene, cyclopentadiene or furane. The addition reaction is appropriately carried out in an inert organic solvent of the abovementioned type, for example of benzene.

If a 3- or 4-amino-phthalic acid, or a salt thereof, is employed as the amine of the formula IIb, it is possible, depending on the reaction conditions, for a 3- or 4-imidylphthalic anhydride to be formed direct during the cyclisation. This anhydride is subsequently converted, again in a manner which is in itself known, into an imidyl derivative, according to the definition, of the formula Ib, for example into the corresponding free acid by hydrolysis or, as indicated above, into the acid chloride or an ester.

The imidyl-benzenedicarboxylic acid derivatives of the formula Ia and Ib are obtained in the form of colourless to pale yellowish crystals and can be isolated, and purified, in a customary manner, for example by extraction and/or recrystallisation from suitable organic solvents, such as benzene, methanol, glacial acetic acid, ethyl acetate, cyclohexane, dioxane or methylene chloride or mixtures of such solvents.

The imidyl derivatives, according to the invention, of the formula Ia and Ib are suitable for the manufacture of crosslinkable polymers, and especially for the manufacture of polycondensation products, the imidyl derivatives being reacted in a manner which is in itself known with substantially stoichiometric amounts of diamines, diols or aminoalcohols or derivatives thereof and optionally in the presence of further di-, tri- or tetra-carboxylic acid derivatives, or functional derivatives thereof.

Crosslinkable polymers can also be obtained by homopolymerisation of compounds of the formula Ia or Ib or by copolymerisation of such compounds with vinyl comonomers, such as vinyl chloride, vinylidene chloride, vinyl acetate, styrene and derivatives thereof, methacrylic acid derivatives, acrylonitrile or divinylbenzene.

By suitable choice of the comonomers or of the polycondensation components it is possible to manufacture polymers which have any desired number, and statistical distribution, of the crosslinkable groups and to convert these polymers into polymers which have a degree of crosslinking suited to the particular application. The crosslinkable polymers obtained are distinguished by good processability, and above all by good solubility in customary organic solvents and good fusibility, and can be processed to give shaped articles of very diverse types, such as fibres, thin and thick films and compression mouldings.

EXAMPLE 1

Example 1

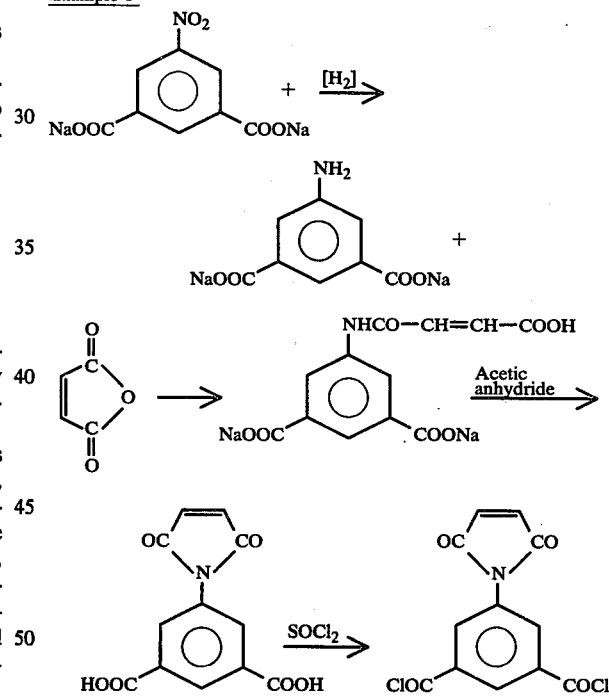

211.2 g (1.0 mol) of 5-nitroisophthalic acid are dissolved in 1,590 g of aqueous sodium hydroxide (90.0 g of sodium hydroxide in 1,500 ml of water) and the solution is rendered neutral with 15 ml of anhydrous acetic acid and hydrogenated in the presence of 10 g of a palladium-on-charcoal catalyst (5% by weight of Pd). The catalyst is filtered off and a solution of 118.0 g (1.2 mols) of maleic anhydride in 150 ml of dioxane is added to the filtrate in the course of 2 hours, whilst stirring vigorously. A white suspension is formed and is stirred overnight at 20°–25° C., 250 ml of acetic acid are then added and the mixture is stirred for a further 2 hours. The amide-acid which has precipitated is filtered off, washed with water and methanol and dried at 30° C. in vacuo for 24 hours. The reaction product (315 g) is then heated, in 2,500 ml of acetic anhydride, whilst stirring, to 80°-85° C. for 30 minutes. About 1.8 liters of liquid (acetic acid + acetic anhydride) are distilled off under a waterpump vacuum. The residual suspension is poured onto 2,000 g of ice and the mixture is stirred overnight. The reaction product which has precipitated is filtered off, washed with water and methanol and dried at 60° C. in vacuo for 12 hours. 210 g of white, crystalline 5-maleimidylisophthalic acid are obtained; melting point > 300° C. (= 80% of theory, based on the nitroisophthalic acid).

NMR spectrum (60 megahertz, dimethylsulphoxide-$d_6$): $\delta$ = 7.23 ppm; 2H (methine protons).

Analysis for $C_{12}H_7NO_6 \times 0.2 H_2O$ (molecular weight 264.79): Calculated: C 54.42%; H 2.85%; N 5.29%; $H_2O$ 1.39%. Found: C 54.16%; H 2.85%; N 5.35%; $H_2O$ 1.39%.

210 g (0.79 mol) of 5-maleimidyl-isophthalic acid in 1,200 ml of thionyl chloride, with the addition of a catalytic amount of pyridine (about 25 drops), are boiled under reflux until a solution has formed (4-7 hours). Excess thionyl chloride is distilled off under reduced pressure. The residue is dissolved in 2 liters of a hot solvent mixture of cyclohexane and benzene (volume ratio 4:1) and the solution is decanted off from a small amount of insoluble resin and left to stand until it crystallises. The reaction product which has precipitated is filtered off and dried at 40° C. in vacuo for 24 hours. 202 g of pale yellowish 4-maleimidyl-isophthalic acid dichloride are obtained; melting point 93°-99° C. A further 7.3 g of the yellowish acid chloride can be isolated from the concentrated mother liquor; melting point 92°-97° C. Total yield = 209 g (70% of theory, based on the 5-nitroisophthalic acid employed).

NMR spectrum (60 megahertz, $CDCl_3$): $\delta$ = 7.00 ppm; 2H (methine protons).

Analysis for $C_{12}H_5NO_4Cl_2$ (molecular weight 298.08): Calculated: C 48.35%; H 1.69%; N 4.70%; Cl 23.79%. Found: C 48.45%; H 1.91%; N 4.71%; Cl 23.48%.

EXAMPLE 2

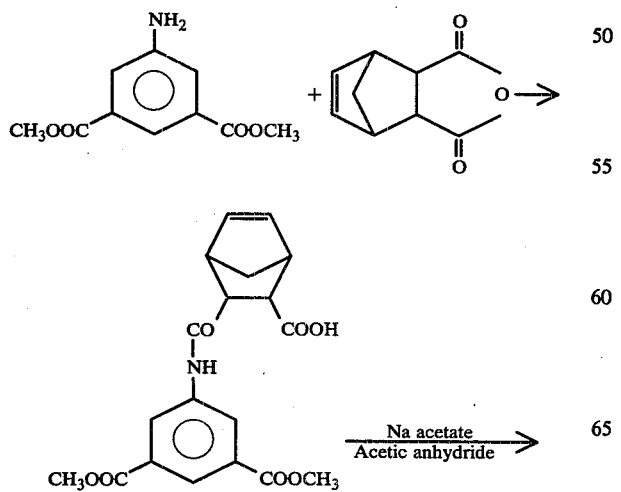

-continued

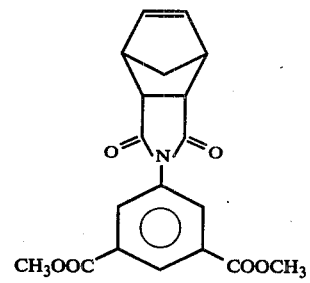

52.3 g (0.25 mol) of 5-amino-isophthalic acid dimethyl ester and 45.1 g (0.25 mol) of nadic anhydride in 600 ml of methylene chloride are kept under reflux for 1 hour. The reaction mixture is then stirred at 20°-25° C. for 3 hours, filtered and dried in vacuo at 50° C. 80 g (85% of theory) of 5-(nadic acid-amidyl)-isophthalic acid dimethyl ester are obtained in the form of a white powder; melting point 155°-158° C.

Analysis for $C_{19}H_{19}NO_7$ (molecular weight 373.36): Calculated: C 61.12%; H 5.13%; N 3.75%. Found: C 60.73%; H 5.07%; N 3.63%.

80 g (0.214 mol) of 5-(nadic acid-amidyl)-isophthalic acid dimethyl ester, together with 4.4 g of anhydrous sodium acetate and 350 ml of acetic anhydride, are warmed to 80° C., whilst stirring, until dissolution is complete (about 30 minutes). The resulting slightly turbid solution is evaporated to dryness in a rotary evaporator. The solid white residue is taken up in methylene chloride and washed twice with saturated sodium bicarbonate solution and twice with water. The organic phase is dried over sodium sulphate and evaporated in a rotary evaporator. 68 g of crude (nadic acid-imidyl)-isophthalic acid dimethyl ester are obtained and are purified by twice extracting by boiling with methanol. 60.1 g of the white imide, which has a melting point of 186°-187° C., remain.

Analysis for $C_{19}H_{17}NO_6$ (molecular weight 355.35): Calculated: C 64.22%; H 4.82%; N 3.94%. Found: C 64.10%; H 4.67%; N 3.99%.

EXAMPLE 3

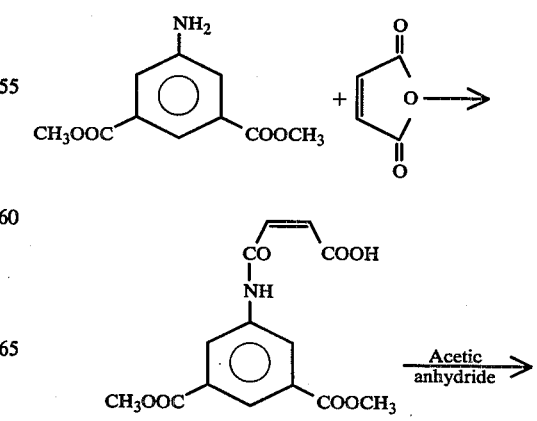

-continued

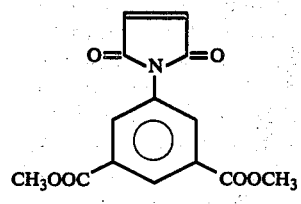

A mixture of 41.8 g (0.2 mol) of 5-amino-isophthalic acid dimethyl ester and 19.6 g (0.2 mol) of maleic anhydride in 500 ml of methylene chloride is stirred for 4 hours at 20°–25° C. The resulting solid product is filtered off and dried overnight at 40° C. 63.8 g of the white amide-acid, which has a melting point 205°–207° C., are obtained and are used further without intermediate isolation.

63.8 g (0.2 mol) of the above amide-acid and 4.4 g of anhydrous sodium acetate in 300 ml of acetic anhydride are warmed to 80° C. for 30 minutes. The resulting yellowish solution is evaporated to dryness in a rotary evaporator. The brownish residue is extracted by boiling with twice 250 ml of methanol. 42.5 g (70% of theory) of 5-maleimidyl-isophthalic acid dimethyl ester, which has a melting point of 188°–190° C., remain.

NMR spectrum (60 megahertz, dimethylsulphoxide-d$_6$) δ = 6.93 ppm/2H (methine protons).

Analysis for C$_{14}$H$_{11}$NO$_6$ (molecular weight 289.24): Calculated: C 58.14%; H 3.84%; N 4.84%. Found: C 57.90%; H 3.88%; N 4.79%.

EXAMPLE 4

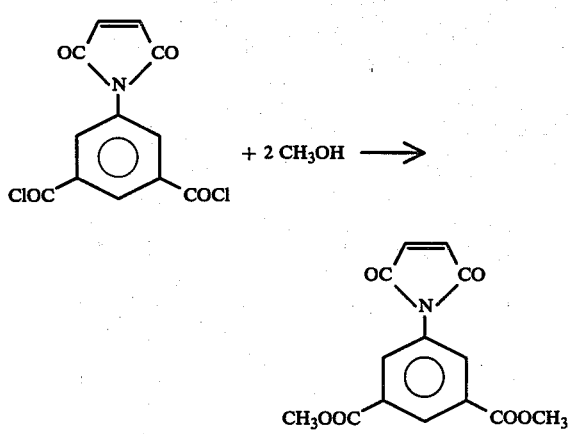

500 ml of methanol are cooled to 5° C. in an ice bath and 60 g (0.2 mol) of the 5-maleimidyl-isophthalic acid dichloride prepared according to Example 1 are added, whilst stirring. The reaction mixture is then stirred for 2 hours, whilst cooling with ice, and the precipitate which has separated out is filtered off and extracted by boiling with 350 ml of methanol. The residue is dried in vacuo at 140° C. 43.2 g (75% of theory) of 5-maleimidyl-isophthalic acid dimethyl ester are obtained; melting point 186°–187° C.

Analysis for C$_{14}$H$_{11}$NO$_6$ (molecular weight 289.24): Calculated: C 58.14%; H 3.84%; N 4.84%. Found: C 57.90%; H 3.83%; N 4.92%.

EXAMPLE 5

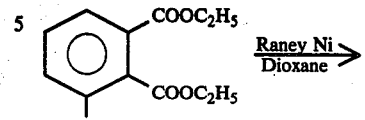

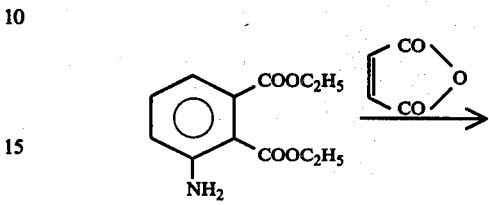

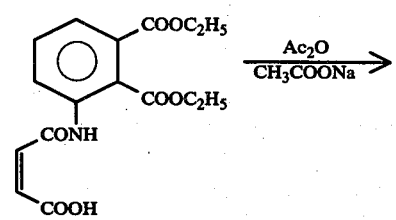

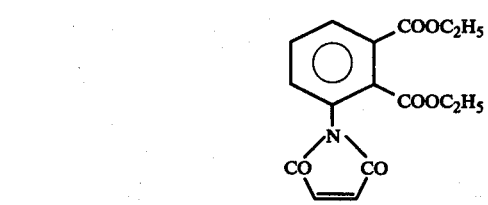

69.7 g (0.26 mol) of 3-nitrophthalic acid diethyl ester in 690 ml of dioxane are hydrogenated in the presence of 7 g of a Raney nickel catalyst to give 3-aminophthalic acid diethyl ester. The reaction solution is filtered and 30.4 g (0.31 mol) of maleic anhydride are added, at room temperature, to the filtrate. The reaction mixture is kept at 25° C. for 12 hours and then concentrated in vacuo. 75 ml of acetic anhydride and 12.7 g of sodium acetate are added to the residue and the mixture is heated to 80° C. for 45 minutes and diluted with 500 ml of water. The crystalline precipitate is rinsed with water and dried in vacuo at 45° C. 68 g (82% of theory) of crystalline 3-maleimidyl-phthalic acid diethyl ester are obtained; melting point 86°–90° C. When the product is recrystallised from ethanol, the melting point rises to 92°–93° C.

Analysis for C$_{16}$H$_{15}$NO$_6$ (molecular weight 317.28): Calculated: C 60.6%; H 4.7%; N 4.4%. Found: C 60.7%; H 4.7%; N 4.5%.

EXAMPLE 6

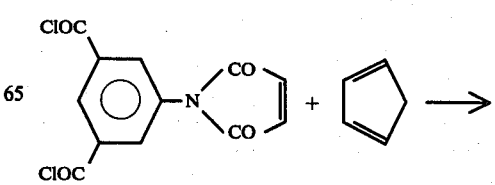

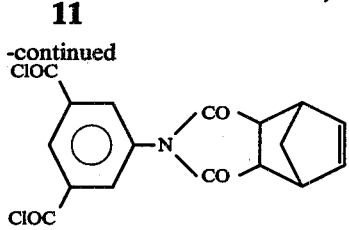

90.0 g (0.3 mol) of the 5-maleimidyl-isophthalic acid dichloride prepared according to Example 1 are dissolved in 900 ml of anhydrous benzene by warming slightly. 30 ml (0.36 mol) of freshly distilled cyclopentadiene are added, whilst stirring. During the addition, the temperature of the reaction mixture rises from 20°–25° C. to 42° C. The reaction mixture is stirred for a further three hours. 600–700 ml of benzene are then distilled off from the resulting pale yellowish solution in a rotary evaporator. Part of the reaction product separates out of the concentrated solution as a white precipitate. 300 ml of anhydrous cyclohexane are added and the reaction mixture is left to stand in an ice bath for several hours. The product which has precipitated is filtered off, washed with a little cyclohexane and dried in vacuo at 40° C. 90.6 g (83% of theory) of white, crystalline 5-(endomethylene-tetrahydrophthalimidyl)-isophthalic acid dichloride are obtained; melting point 162°–164° C.

IR spectrum (CHCl$_3$): $\lambda_{max}$ inter alia 5.65/5.80μ.

Analysis for C$_{17}$H$_{11}$Cl$_2$NO$_4$ (molecular weight 364.18): Calculated: C 56.07%; H 3.05%; N 3.85%; Cl 19.47%. Found: C 56.07%; H 2.95%; N 3.87%; Cl 18.79%.

EXAMPLE 7

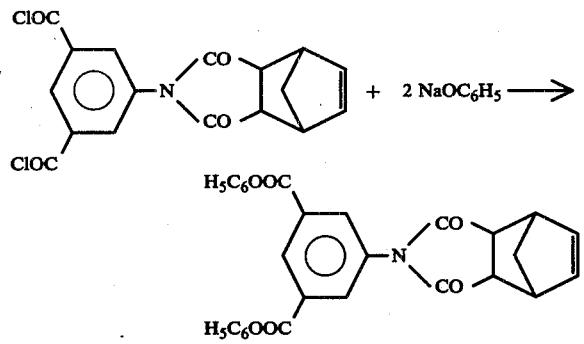

36.42 g (0.1 mol) of the 5-(endomethylene-tetrahydrophthalimidyl)-isophthalic acid dichloride prepared according to Example 6 are added, whilst stirring, to a suspension, which has been cooled to 5° C., of 24.0 g (0.207 mol) of sodium phenolate in 200 ml of ethyl acetate. During the addition the temperature of the reaction mixture rises to 45° C. The suspension is stirred at 70° C. for 2 hours, then cooled to 20°–25° C. and filtered. The filter residue is suspended in methylene chloride, the suspension is centrifuged and the slightly turbid supernatant liquor is separated off, sodium bisulphate hydrate is added to this liquor and the mixture is shaken for 20 minutes. The resulting clear solution is percolated through a short column of silica gel and evaporated in a rotary evaporator. A little diethyl ether is added to the residue, whereupon the product crystallises out. In an analogous manner, the filtrate from the abovementioned filtration is evaporated in a rotary evaporator, the residue is taken up in methylene chloride and the mixture is percolated through the column of silica gel and evaporated in a rotary evaporator and diethyl ether is added to the residue, whereupon crystallisation again takes place. The two mixtures containing the crystalline products are combined and filtered and the residue is dried in vacuo at 100° C. 26.1 g (54.5% of theory) of crystalline 5-(endomethylene-tetrahydrophthalimidyl)-isophthalic acid diphenyl ester, which has a melting point of 184°–185° C., are obtained.

IR spectrum (CHCl$_3$): $\lambda_{max}$ inter alia 5.75/8.85μ.

Analysis for C$_{29}$H$_{21}$NO$_6$ (molecular weight 479.49): Calculated: C 72.64%; H 4.41%; N 2.92%. Found: C 72.59%; H 4.37%; N 2.76%.

EXAMPLE 8

Copolyamide of:

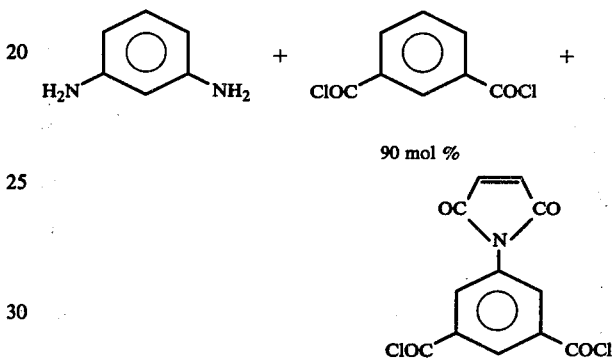

(a) Preparation of the acid chloride mixture 219.26 g (1.08 mols) of isophthalic acid dichloride and 35.78 g (0.12 mol) of 5-maleimidyl-isophthalic acid dichloride are melted together at 70° C., the melt is allowed to solidify and the solid is then crumbled.

(b) Condensation 107.35 g (0.993 mol) of m-phenylenediamine are dissolved in 950 ml of N,N-dimethylacetamide (DMA), the solution is cooled to $\leq -20°$ C. in a bath of solid carbon dioxide and 212.70 g (1.0 mol) of the above acid chloride mixture, in the solid form, are added all at once, whilst stirring. The cooling bath is removed, whereupon the reaction solution warms to 30°–50° C., dimethylacetamide hydrochloride separating out and the viscosity increasing sharply. The temperature is kept below 50° C. by means of an ice bath. The reaction mixture is then allowed to cool to 27° C. and the highly viscous reaction product is stirred for a further 2 hours. The resulting polymer is precipitated, if appropriate after diluting with N,N-dimethylacetamide, in a mixer by means of water and the precipitate is washed with water until neutral and dried at 120° C. in a vacuum drying cabinet for 24 hours. A pale yellowish, fibrous, crosslinkable copolyamide which has an inherent viscosity $\eta_{inh.}$ of 1.21 dl/g (0.5% by weight in DMA at 25° C.) is obtained in quantitative yield. It is soluble in N,N-dimethylacetamide and N,N-dimethylformamide without additives, such as lithium chloride, and is suitable for the manufacture of films and fibres in a manner which is in itself known.

The polymer can be crosslinked, for example by heating to 200° C. or by irradiation with UV light.

For compression moulding, the copolyamide which was obtained according to the above example and dried in vacuo is introduced into a compression mould for standard bars, which is heated to 320° C. The pressure is raised to 1,000 kg/cm² in the course of one minute and is maintained at the above temperature for 5 minutes. After release from the mould, transparent mouldings which have good flexural strength are obtained.

EXAMPLE 9

10.91 g (0.1 mol) of p-aminophenol are dissolved in 200 ml of DMA. The solution is cooled to −20 C. 10.15 g (0.05 mol) of solid isophthalic acid dichloride are added, whilst stirring vigorously, and the reaction mixture is stirred for a further 10 minutes. 20.2 g (0.2 mol) of triethylamine are then added, the mixture is again cooled to −20° C. and 14.91 g (0.05 mol) of 5-maleimidyl-isophthalic acid dichloride are added. The cooling bath is removed and the reaction mixture is stirred for a further 2 hours. The hydrochloride is separated off by filtration. The resulting polymer is precipitated in water and dried at 100° C. under a high vacuum. A brownish coloured product which has an inherent viscosity of 0.59 dl/g (0.5% by weight in DMA at 25° C.) is obtained and can be crosslinked by heating to 200° C. for several hours.

EXAMPLE 10

7.93 g (0.04 mol) of 4,4'-diaminodiphenylmethane are dissolved in 200 ml of anhydrous DMA, under a nitrogen atmosphere, in a sulphonation flask. This solution is cooled to −15° C. to −20° C. A mixture of 10.31 g (0.032 mol) of 3,3', 4,4'-benzophenonetetracarboxylic acid dianhydride and 2.38 g (0.008 mol) of 5-maleimidyl-isophthalic acid dichloride in the solid form is then added in portions and whilst stirring the reaction mixture. The means of cooling are removed after 30 minutes and the solution is stirred for a further 1 hour at 20–25° C. and, in order to produce films, is cast onto aluminium foils and heated as follows: 4 hours at 80° C./20 mm Hg, 30 minutes each at 100° C./20 mm Hg, 120° C./20 mm Hg, 140° C./20 mm Hg, 160° C./10⁻¹ mm Hg, and 180° C./10⁻¹ mm Hg and 1 hour at 200° C./10⁻¹ mm Hg. After dissolving off the aluminium foil with dilute hydrochloric acid, transparent flexible films of good mechanical strength are obtained.

EXAMPLE 11

A mixture of 18 g (0.2 mol) of 1,4-butanediol, 28.9 g (0.1 mol) of 4-maleimidyl-phthalic acid dimethyl ester and 0.045 g of calcium acetate is heated to 100° C. for 12 hours, whilst stirring and passing nitrogen through the mixture. After cooling, the reaction mixture is diluted with 300 ml of chloroform, 20.3 g (0.1 mol) of isophthalic acid dichloride are added in portions and the mixture is heated under reflux for 2 hours. In order to produce films, the resulting polymer solution is cast onto an aluminium foil and the solvent is evaporated in a vacuum oven.

EXAMPLE 12

31.2 g (0.3 mol) of styrene, 10 g (0.035 mol) of 5-maleimidyl-isophthalic acid dimethyl ester and 0.1 g of α,α'-azo-isobutyronitrile are dissolved in 300 ml of DMA and the solution is warmed to 60° C. under a nitrogen atmosphere. The resulting reaction solution is stirred at this temperature for 8 hours. The solvent is distilled off. The residue is extracted by boiling three times with benzene and dried in vacuo at 100° C.

Elementary analysis shows that a copolymer which contains 50 mol % of 5-maleimidyl-isophthalic acid dimethyl ester has been formed.

EXAMPLE 13

43.02 g (0.18 mol) of sebacic acid dichloride are added dropwise to 18 g (0.2 mol) of 1,4-butanediol, whilst passing nitrogen through the mixture and stirring vigorously. During the addition the internal temperature is kept below 70° C. by cooling. The reaction mixture is then warmed to 100° C. and 5.96 g (0.02 mol) of 5-maleimidyl-isophthalic acid dichloride in the solid form are added and the mixture is then stirred for 30 minutes under normal pressure and subsequently for 30 minutes under a waterpump vacuum. On cooling, the polycondensate solidifies to an opaque mass which has a softening point of about 65° C.

100 mg of α,α'-azo-isobutyronitrile are added to 20 ml samples of, respectively, a 10% strength, 20% strength and 50% strength solution of the above polymer in styrene and the mixtures are kept at 70° C. for 24 hours under nitrogen. An opaque insoluble moulding is obtained.

EXAMPLE 14

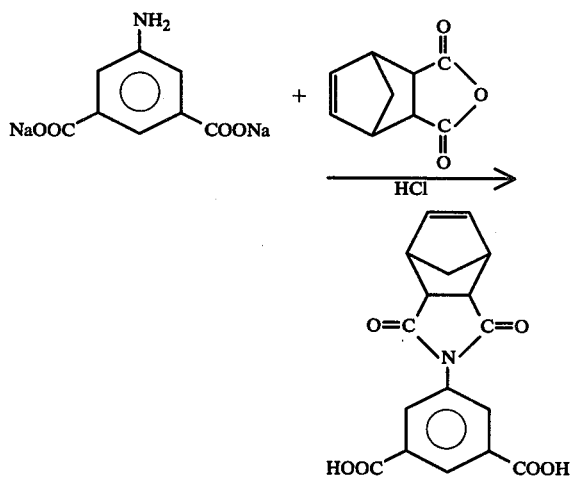

9.0 g (0.225 mol) of sodium hydroxide are dissolved in 150 ml of water. 21.12 g (0.1 mol) of 5-nitro-isophthalic acid are then added and the solution is buffered to neutral with about 1.8 ml of anhydrous acetic acid. The solution is then hydrogenated at 20–25° C. using Raney nickel or palladium as the catalyst (hydrogen absorption = 100% of theory). The catalyst is separated off from the hydrogenated solution by filtration. 16.5 g (0.1 mol) of powdered nadic anhydride are added to the resulting clear, colourless filtrate and the reaction mixture is heated (internal temperature 90–95° C.), whilst stirring, for 2 hours in an oil bath which has a bath temperature of 110° C. A clear solution is formed and is allowed to cool to 20–25° C. Traces of undissolved substance are filtered off. 20 ml of concentrated hydrochloric acid (about 37% strength) are then added dropwise, whilst stirring. The resulting fine white precipitate is filtered off, washed with water and dried in vacuo at 80° C. for 24 hours. 30.8 g (94% of theory) of 5-(nadic acid-imidyl)-isophthalic acid are obtained; melting point > 300° C.

IR spectrum (Nujol): $\lambda_{max}$ inter alia 5.80μ.

29.7 g (0.091 mol) of the above 5-(nadic acid-imidyl)-isophthalic acid are refluxed with 100 ml of thionyl chloride, with the addition of 3 drops of N,N-dimethylformamide, for 5 hours. The resulting slightly turbid solution is filtered, the filtrate is evaporated in a rotary evaporator, the greenish solid residue is taken up in 100 ml of hot xylene, a little active charcoal is added and the mixture is filtered hot. 50 ml of cyclohexane are also added to the crystallising filtrate. The filtrate is then allowed to crystallise out overnight in a refrigerator. The resulting colourless crystals are filtered off and dried in vacuo at 80° C. 28.0 g (85% of theory) of 5-(nadic acid-imidyl)-isophthalic acid dichloride, which has a melting point of 165-168° C. are obtained.

IR spectrum (CHCl₃): $\lambda_{max}$ inter alia 5.65/5.80μ.

The product is identical to the substance obtained by an addition reaction of cyclopentadiene with 5-maleimidylisophthalic acid dichloride (compare Example 6).

We claim:

1. A compound of the formula

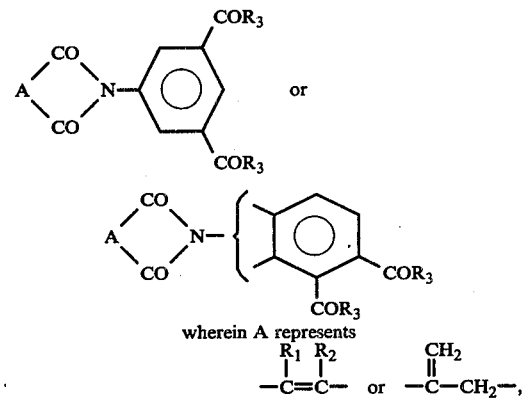

wherein A represents $$-\overset{R_1}{\underset{|}{C}}=\overset{R_2}{\underset{|}{C}}- \quad \text{or} \quad -\overset{CH_2}{\underset{\|}{C}}-CH_2-,$$

$R_1$ and $R_2$ independently of one another denote hydrogen, chlorine or bromine, and $R_3$ denotes chlorine, hydroxyl, phenoxy; phenoxy substituted by one or two nitro groups, by one alkyl of 1 to 2 carbon atoms, by one alkoxy of 1 to 2 carbon atoms or by two to five halogen atoms; alkoxy with 1 to 18 carbon atoms or an $-O^-M^+$ group, in which $M^+$ represents an alkali metal cation, a trialkylammonium cation with 3 to 24 carbon atoms or a quaternary ammonium cation.

2. An imidyl-benzenedicarboxylic acid derivative of the formula Ia or Ib according to claim 1, wherein A represents the radical —CH=CH—.

3. An imidyl-benzenedicarboxylic acid derivative of the formula Ia or Ib according to claim 1, wherein $R_3$ represents a chlorine atom, an unsubstituted phenoxy group or an alkoxy group with 1-12 carbon atoms.

4. An imidyl-benzenedicarboxylic acid derivative of the formula Ia according to claim 1, wherein A represents the radical —CH=CH— and $R_3$ represents a chlorine atom.

5. The compound as claimed in claim 1, having the formula

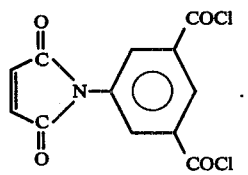

6. The compound as claimed in claim 1, having the formula

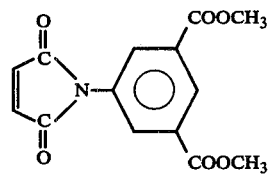

7. The compound as claimed in claim 1, having the formula

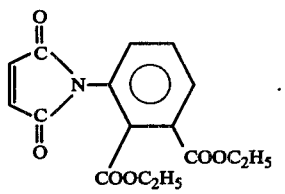

* * * * *